United States Patent
Koshimizu et al.

[19]

[11] Patent Number: 5,928,532
[45] Date of Patent: Jul. 27, 1999

[54] METHOD OF DETECTING END POINT OF PLASMA PROCESSING AND APPARATUS FOR THE SAME

[75] Inventors: Chishio Koshimizu, Yamanashi-ken; Susumu Saito, Kofu, both of Japan

[73] Assignee: Tokyo Electron Limited, Tokyo, Japan

[21] Appl. No.: 08/962,736

[22] Filed: Nov. 3, 1997

[30] Foreign Application Priority Data

Nov. 11, 1996 [JP] Japan .................................. 8-298697

[51] Int. Cl.$^6$ ............................ B23K 10/00; B44C 1/22; G01N 21/00
[52] U.S. Cl. ................................ 219/121.42; 219/121.41; 219/121.59; 156/345; 156/646.1; 216/60; 356/316
[58] Field of Search ........................... 219/121.41, 121.4, 219/121.43, 121.59, 121.42; 156/345, 643.1, 646.1; 356/316, 72; 216/60; 204/192.13, 298.03, 298.32

[56] References Cited

U.S. PATENT DOCUMENTS

| | | |
|---|---|---|
| 4,289,188 | 9/1981 | Mizutani et al. . |
| 4,491,499 | 1/1985 | Jerde et al. . |
| 5,097,430 | 3/1992 | Birang ..................................... 156/345 |
| 5,320,704 | 6/1994 | Horioka et al. ...................... 156/643.1 |
| 5,322,590 | 6/1994 | Koshimizu . |
| 5,565,114 | 10/1996 | Saito et al. . |

FOREIGN PATENT DOCUMENTS

63-81929   4/1988   Japan .

*Primary Examiner*—Mark H. Paschall
*Attorney, Agent, or Firm*—Oblon, Spivak, McClelland, Maier & Neustadt, P.C.

[57] ABSTRACT

When processing using a plasma is performed for an object to be processed, a photodetecting unit sequentially detects emission of two active species having specific wavelengths in a designated period during the processing. On the basis of the emission detection information of the two active species, two approximate expressions of linear functions are obtained in the relationship between the emission intensity and time. The ratio of the two approximate expressions of linear functions and the derivative of the ratio are obtained to form a graph in which the ratio is plotted on the abscissa, the derivative of the ratio is plotted on the ordinate, and the intersection between the average value of the ratio and the average value of the derivative of the ratio is the origin. The ratio and the derivative of the ratio are obtained by using the emission detection information of the two active species during the processing after the designated period. The end point of the plasma processing is determined when the position of the ratio and the derivative of the ratio thus obtained deviates from a predetermined region in the graph.

11 Claims, 9 Drawing Sheets

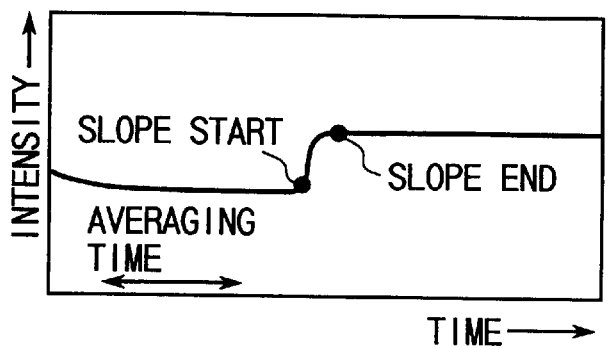
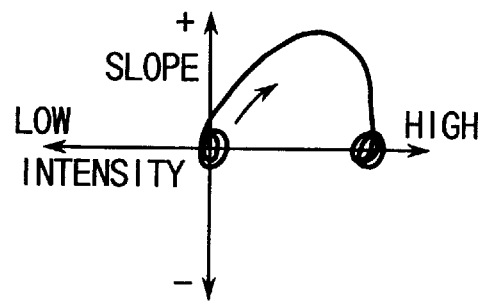
FIG. 7A　　　　　　　FIG. 7B
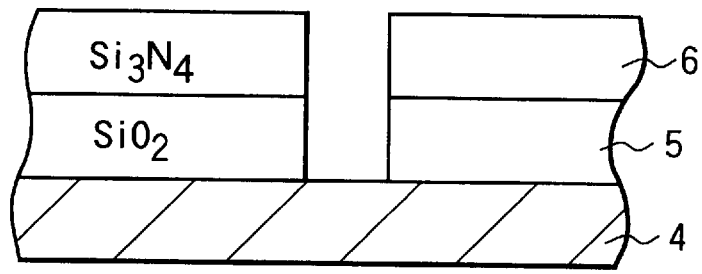
FIG. 8
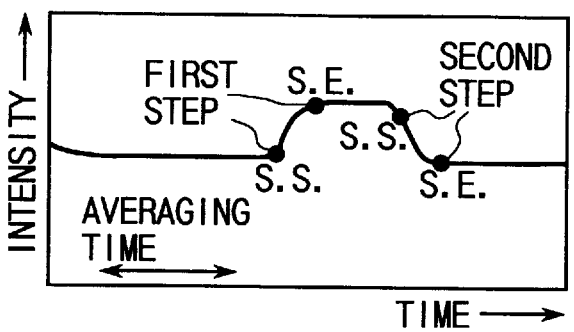
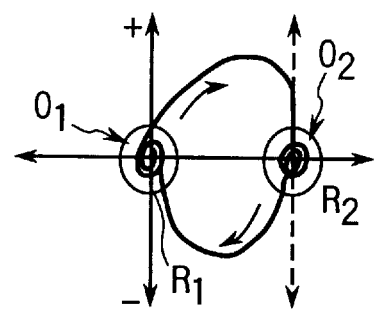
FIG. 9A　　　　　　　FIG. 9B

METHOD OF DETECTING END POINT OF PLASMA PROCESSING AND APPARATUS FOR THE SAME

BACKGROUND OF THE INVENTION

The present invention relates to a method of detecting the end point of plasma processing and an apparatus for the same.

A plasma processing apparatus, particularly, an etching apparatus is conventionally extensively used in semiconductor fabrication steps or manufacturing steps of substrates for liquid crystal displays. For example, an etching apparatus of this sort includes upper and lower electrodes arranged parallel to each other. The etching apparatus generates a plasma from an etching gas by discharge between the upper and lower electrodes and uses the resultant active species to etch an object to be processed, i.e., a film such as an oxide film formed on a semiconductor wafer. In this etching processing, it is desirable to perform the processing in accordance with a predetermined pattern by monitoring the progress of the etching and accurately detecting process the end point of the etching.

Conventionally, methods of instrumental analysis such as mass analysis and spectrochemical analysis are used as methods of detecting the end point of etching process. Of these methods, spectrochemical analysis which is relatively simple and has high sensitivity is widely used. When the method of spectrochemical analysis is used in detecting the end point of etching process, a practical approach is to select a predetermined type of active species from active species such as radicals or ions of an etching gas and its decomposition or reaction products and measure a change in the emission intensity of the selected active species with time. The active species to be selected changes in accordance the type of etching gas or the material to be etched. For example, when a silicon oxide film is to be etched by using a fluorocarbon-based etching gas such as $CF_4$, $CO^*$ which is a reaction product of $CF_4$ and abruptly decreases its emission intensity at the end point is used. One known method is to measure (by using only one wavelength) only the emission intensity (by using a wavelength of 219 nm or 483.5 nm) of $CO^*$ with respect to time, and compare changes in the emission intensity and, e.g., the first and second derivatives of the intensity with respect to time, thereby determining the end point of etching process. Another known method as disclosed in Jpn. Pat. Appln. KOKAI Publication No. 63-81929 is to measure the emission intensity of $CO^*$ with respect to time and the emission intensity of two-wavelength reference light (in Jpn. Pat. Appln. KOKAI Publication No. 63-81929, an atom such as helium whose emission spectral intensity has wavelengths of 706.5 nm and 667.8 nm), and compare changes in the emission intensity ratio or, e.g., the first and second derivatives of the ratio with respect to time, thereby determining the end point of etching. Another known example of the method using two wavelengths is, as disclosed in Jpn. Pat. Appln. KOKAI Publication No. 5-29276 (corresponding to U.S. Pat. No. 5,322,590), to measure the emission intensity of $CO^*$ with respect to time and the emission intensity of $CF^*$, instead of the reference light described above, as a decomposition product of an etching gas whose emission intensity abruptly rises at the end point, and compare changes in the ratio of the emission intensities or, e.g., the first and second derivatives of the ratio with respect to time, thereby determining the end point of etching process.

The conventional end point detection method using a single wavelength cannot accurately detect the end point of plasma processing because the end point becomes indistinct due to emission intensity variations caused by, e.g., fluctuation of a plasma. The conventional end point detection methods using two wavelengths do not take account of the fact that a change in the emission intensity of $CO^*$ as an active species of a reaction product and a change in the emission intensity of reference light or $CF^*$ as a decomposition product of an etching gas, which abruptly raises its emission intensity at the end point, with respect to the end-point time are different due to, e.g., fluctuation of a plasma, a temperature change in a chamber, an electrode, or a wafer, or a deposition sticking to the wall of the chamber. That is, the methods simply obtain the ratio of the two emission intensities and detect the end point by using the ratio. Accordingly, end point detection is difficult to accurately perform.

In U.S. Pat. No. 5,565,114, the present inventors have disclosed an idea by which when the end point of etching process is to be detected by using the emission intensity ratio of two wavelengths, the ratio of the two emission intensities is obtained after changes in the emission intensities with time are matched (i.e., after the slopes of curves representing changes in the two emission intensities with time are matched). When the ratio of the two emission intensities is monitored after the slopes of change curves of the two emission intensities are matched in advance as disclosed in this publication (U.S. Pat. No. 5,565,114), the end point can be detected more accurately than when the ratio of the two emission intensities is simply monitored. Unfortunately, the method of matching the slopes of the two emission intensities disclosed in this U.S. patent calculates average values of change curves of the emission intensities in a designated interval before the end point, and calculates a total sum of absolute values of the differences between the emission intensities and the average values in the designated interval for the two change curves. Since the method uses this total sum (i.e., calculates an area), the method is weak against noise.

BRIEF SUMMARY OF THE INVENTION

It is an object of the present invention to provide a method of detecting the end point of plasma processing, which can accurately detect the end point by permitting variations in the plasma condition, and an apparatus for the same.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 7A is a graph showing another example of the changes in the emission intensity (ratio) and the slope (derivative) with time, and FIG. 7B is a graph in which the emission intensity (ratio) and the slope (derivative) shown in FIG. 7A are plotted on the abscissa and the ordinate, respectively;

FIG. 8 is a sectional view showing one example of an object to be etched;

FIG. 9A is a graph, similar to FIG. 7A, showing still another example of the changes in the emission intensity (ratio) and the slope (derivative) with time, and FIG. 9B is a graph in which the emission intensity (ratio) and the slope (derivative) shown in FIG. 9A are plotted on the abscissa and the ordinate, respectively;

DETAILED DESCRIPTION OF THE INVENTION

An embodiment of the present invention will be described in detail below with reference to the accompanying drawings.

During plasma processing, a plasma is in an unstable state (fluctuation of a plasma) because it is affected by various conditions such as applied power, gas flow rate, pressure, and plasma temperature. Accordingly, the intensity of emission of an active species used in detecting the end point of the plasma processing is also unstable.

Figure 1:
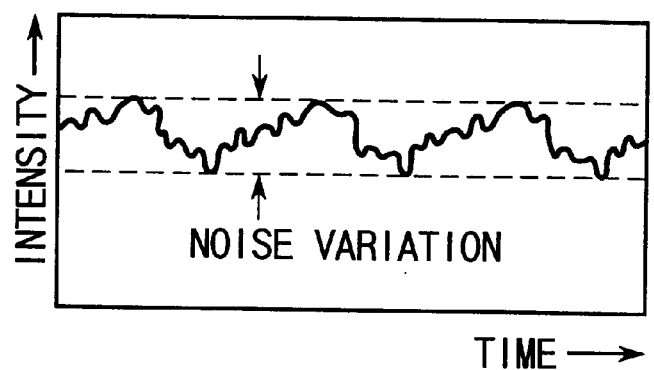
FIG. 1 is a graph for explaining noise variations in plasma emission intensity.
Figure 2:
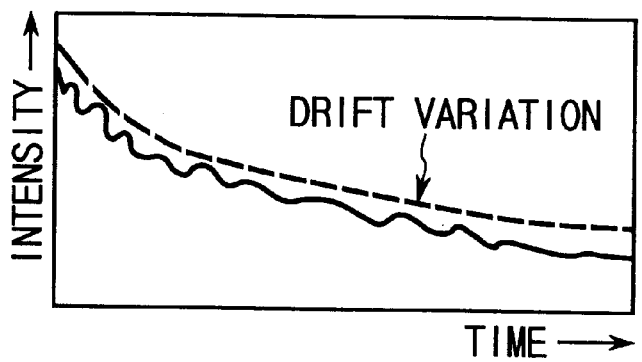
FIG. 2 is a graph for explaining drift variations in plasma emission intensity.

Variations in the emission intensity have two elements, i.e., periodic or single noise variations as shown in FIG. 1 and drift variations which gradually increase or decrease with time as shown in FIG. 2. In FIGS. 1 and 2, the ordinate indicates the emission intensity, and the abscissa indicates time. It is known that the noise variations are primarily caused by slight variations in RF power, gas flow rate, or pressure, and the drift variations are primarily caused by variations in plasma temperature with time.

As disclosed in Jpn. Pat. Appln. KOKAI Publication Nos. 63-81929 and 5-29276, it is basically possible to remove the noise variation since common variation components can be canceled out by calculating the intensity ratio of two wavelengths. However, when the ratios of emission from an active species to reference light or another active species are simply calculated and compared, variation components cannot be well removed if drifts (slopes of waveforms as a whole) are different.

The present inventors have extensively studied the above problem and found that it is possible to remove the drift variations and accurately perform end point detection by comparing change amounts while time-wise matching derivatives of the emission intensities of light having two wavelengths as disclosed in U.S. Pat. No. 5,565,114. However, as already described in "BACKGROUND OF THE INVENTION", the method of time-wise matching derivatives of the emission intensities of light having two wavelengths (i.e., the method of matching the slopes of emission intensity change curves of the two wavelengths) disclosed in U.S. Pat. No. 5,565,114 has a drawback of being weak against noise because the method uses area calculations. The present inventors, therefore, have taken this drawback into consideration and further improved the method of matching the slopes of emission intensity change curves of two wavelengths and thereby increased the accuracy of end point detection.

An end point detection method of the present invention will be described in detail below.

Figure 3:
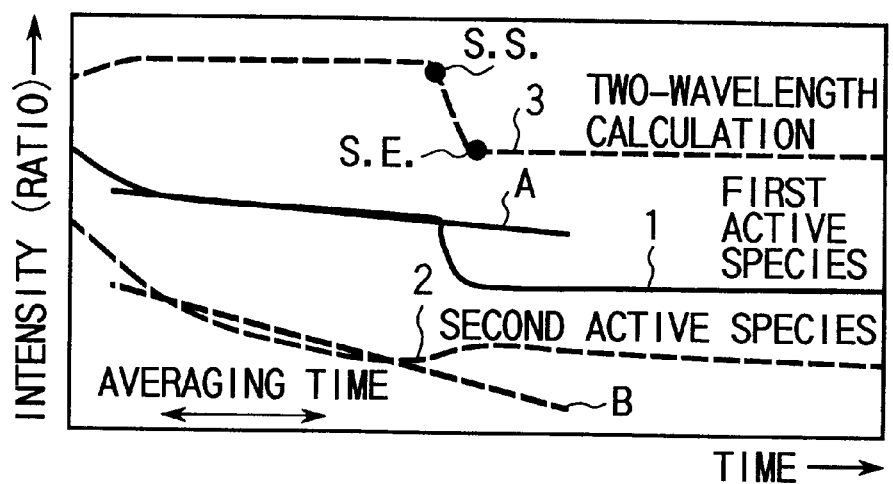
FIG. 3 is a graph for explaining approximate expressions of linear functions of first and second active species and an affine approximate expression of linear function of the first active species.

First, in performing processing using a plasma for an object to be processed, the emission intensities of first and second active species respectively having specific wavelengths (e.g., peak wavelengths) in a designated period (averaging time) are sequentially detected during the plasma processing by using a photodetecting means. Subsequently, on the basis of the emission detection information (i.e., changes in the emission intensities with time) of the first and second active species in the averaging time, an approximate expression of linear function A of the first active species and an approximate expression of linear function B of the second active species in the relationship between the emission intensity and time are obtained. That is, as shown in FIG. 3 in which the emission intensity is plotted on the ordinate and time is plotted on the abscissa, by using emission intensity change waveform 1 of the first active species and emission intensity change waveform 2 of the second active species in the averaging time, experimental formulas are obtained by the method of least squares. In the present invention, the approximate expressions of linear functions A and B (equations 1 and 2) are obtained as experimental formulas $$Y_1 = a_1 \times X + b_1 (A) \quad (1)$$

$$Y_2 = a_2 \times X + b_2 (B) \quad (2)$$

(where $Y_1$ and $Y_2$ represent the emission amounts of the first and second active species, respectively, X represents the elapsed time, $a_1$ and $a_2$ represent linear coefficients, and $b_1$ and $b_2$ represent Y-intercepts.)

Subsequently, an affine approximate expression of linear function A' of the first active species is obtained from the approximate expression of linear function A of the first active species and the approximate expression of linear function B of the second active species. That is, the affine approximate expression of linear function A' (equation 3) is obtained by substituting X of equation 2 into X of equation 1

$$Y = (a_1/a_2) \times (Y_2 - b_2) + b_1(A') \quad (3)$$

Both equations (1) and (3) represent the emission amount $Y_1$ of the first active species, and the ratio (A/A') (a curve denoted by reference numeral 3 for reference in FIG. 3) is calculated. Furthermore, the derivative (d(A/A')/dt) of the ratio (A/A') is calculated. Note that the ratio (A/A') is nearly 1 when the two active species show similar tendencies (features) of emission intensity changes and becomes larger than 1 as the tendencies become different from each other. That is, when the two active species show different tendencies, as shown in FIG. 3, the value of the ratio is constant before the end point (before slope start: S.S. to be described later), largely changes (increases or decreases) at the end point, and again becomes constant after the end point (after slope end: S.E. to be described later). Although the term "end point" is herein used for convenience, it is to be understood from FIG. 3 and the following description that this term indicates a predetermined period (time from S.S. to S.E.), rather than a moment.

Subsequently, the end point is determined on the basis of the above results.

As described above, the waveform of the ratio (A/A') remains constant (does not change with time) before and after the end point. Therefore, by setting a threshold value between these two fixed values (before and after the end point), the end point can be easily detected by detecting this threshold value. However, in end point detection like this, if the threshold value is set very close to the start or end of a change in the waveform of the ratio (A/A'), it is sometimes impossible to stably detect the end point. Accordingly, it is desirable to set the threshold value in a period between S.S. and S.E. and slightly apart from the two points.

In the present invention, the end point can be accurately determined by accurately detecting the start (slope start: S.S.) and the end (slope end: S.E.) of a change as described above.

Figure 4:
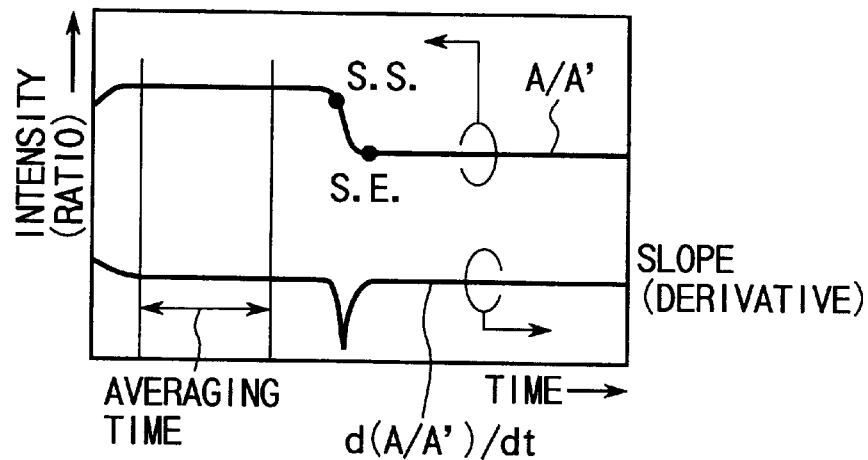
FIG. 4 is a graph showing changes in emission intensity (ratio) and slope (derivative) with time.

FIG. 4 shows changes with time in the ratio (A/A') of emission intensities calculated as above and its derivative, i.e., the slope (d(A/A')/dt). As shown in FIG. 4, the ratio (A/A') is constant before the end point, largely decreases at the end point, and again becomes constant after the end point. The slope (d(A/A')/dt) is constant before the end point, shows a large decrease or peak at the end point, and again becomes constant after the end point as before the end point.

Figure 5:
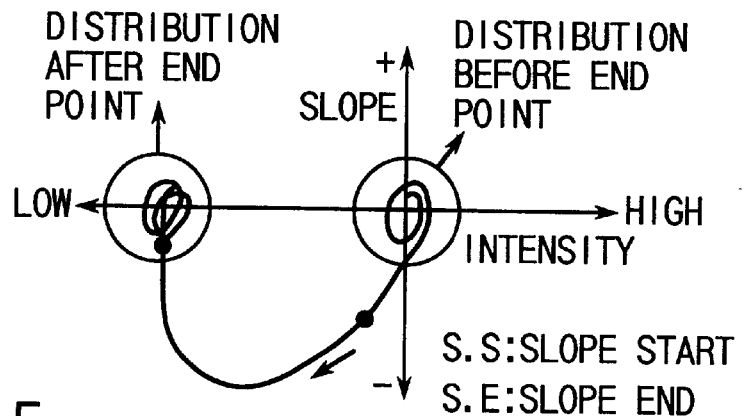
FIG. 5 is a graph in which the emission intensity (ratio) and the slope (derivative) shown in FIG. 4 are plotted on the abscissa and the ordinate, respectively.

FIG. 5 shows a graph of a two-dimensional coordinate system in which the ratio (A/A') of the emission intensities is plotted on the abscissa, the derivative (d(A/A')/dt) of the ratio is plotted on the ordinate, and the intersection between the average value of the ratio (A/A') and the average value of the derivative (d(A/A')/dt) of the ratio is the origin. As can be seen from FIG. 5 in which the passing of time is indicated by a curve, the values distribute in the center of the coordinate system before the end point. When a change starts near the end point, the values largely protrude into the first quadrant or the third quadrant (in FIG. 5, the third quadrant) of the coordinate system. After the end point, the values come close to the abscissa and distribute near the abscissa. By thus expressing the values on a two-dimensional coordinate system, it is possible to visualize the relationship between the ratio (A/A') and the derivative (d(A/A')/dt) of the ratio and changes in the states of the respective wavelengths. For example, these data can be seen as images through program processing.

In determining the end point, the average values and variances of the ratio (A/A') and the derivative (d(A/A')/dt) of the ratio in the averaging time are obtained. The averaging time is set in a period before the end point of plasma processing. Note that the start point of the averaging time is preferably set at a timing at which the plasma is stabilized, rather than the plasma processing start timing.

Subsequently, the initial variation range (predetermined region) in the graph is obtained from predetermined values (to be described below) calculated from the information of the variances of the ratio (A/A') and the derivative (d(A/A')/dt) of the ratio.

Figure 6:
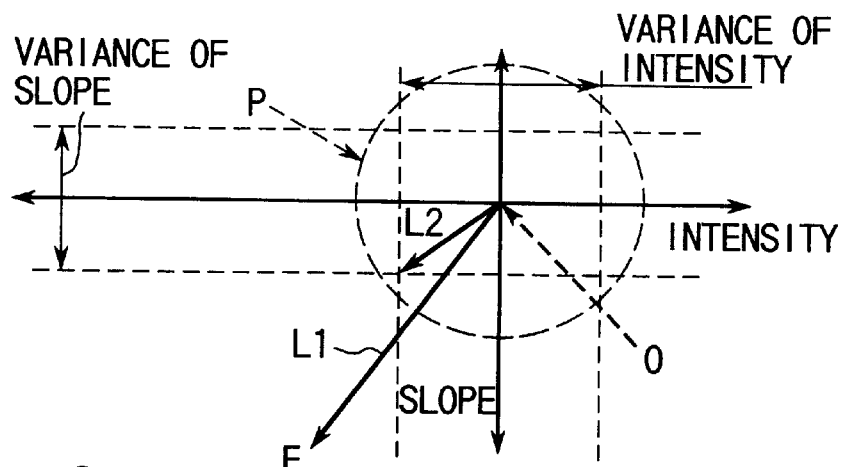
FIG. 6 is a graph for explaining slope start.

As shown in FIG. 6, this variation range (predetermined region) is preferably set by a root-sum-square value $r_1$ of a predetermined value of the ratio (A/A') and a predetermined value of the derivative (d(A/A')/dt) of the ratio calculated from the information of the variances in the designated period (averaging time). In effect, a root-sum-square value $$\left\{ \sqrt{[(\text{predetermined value of ratio})^2 + (\text{predetermined value of slope (derivative of ratio})^2]} \right\}$$

(C) of the predetermined values of the ratio (A/A') and the derivative (d(A/A')/dt) of the ratio calculated from the variance information is obtained. The variation range is a circular range indicated by a dotted line P having the root-sum-square value thus calculated as a radius and the average values as an origin O. Accordingly, a large number of values distribute in this circle P before the end point. When a change begins near the end point, the values gradually move away from the circle. The maximum value of the differences between the ratio (A/A') and the average value of the ratio can be used as the predetermined value of the ratio calculated from the variance information. Also, the maximum value of the differences between the derivative (d(A/A')/dt) of the ratio and the average value of the derivative of the ratio can be used as the predetermined value of the derivative of the ratio calculated from the variance information.

On the basis of the above fact, the slope start is determined when the variation range is exceeded.

However, the slope start cannot be accurately determined near the variation range. Therefore, a position (value) (indicated by symbol E) at which the end point is determined is set outside the variation range in the graph. The slope start is determined by comparing a distance L1 from the set position to the origin with a radius L2 of the circle of the variation range. That is, the ratio (A/A') and the derivative (d(A/A')/dt) of the ratio is obtained by using the emission detection information of the first and second active species during the processing after the averaging time. The distance L1 from the position to the origin in the graph is then obtained. This distance is compared with the radius L2 of the variation range obtained from the emission detection information in the averaging time.

More specifically, a root-sum-square value $$\left\{ \sqrt{[(\text{ratio} - \text{average value of ratio})^2 + (\text{slope} - \text{average value of slope})^2]} \right\}$$

(D) of the differences between the ratio (A/A') and the derivative (d(A/A')/dt) of the ratio corresponding to the position at which the end point is determined and the respective average values (origin) is obtained.

The slope start is determined when the ratio (D/C) of this root-sum-square value (D) to the root-sum-square value (C) described above exceeds a preset threshold value.

On the other hand, the slope end is determined when the derivative (d(A/A')/dt) of the ratio, i.e., the slope again comes close to the abscissa (to the variation range of the slope). That is, the slope for determining the end point is compared with a predetermined value obtained from the variance of the slope, thereby obtaining ((slope—average value of slope)/predetermined value). The slope end is determined when this value becomes smaller than a preset threshold value. Note that the predetermined value obtained from the variance is calculated as described above.

When the slope end is used in end point detection, the end point of plasma processing is determined when the position of the ratio (A/A') and the derivative (d(A/A')/dt) of the ratio obtained by using the emission detection information of the first and second active species during the processing after the designated period deviates from the origin and again comes close to the abscissa in the graph.

As in the case where the slope start is used in end point detection, it is also possible to set a variation range. If this is the case, the ratio and the derivative of the ratio are obtained by using the emission detection information of the first and second active species during the processing after the designated period, and another end point of the plasma processing is determined when the position of the ratio and the derivative of the ratio thus obtained enters the variation range (predetermined region). Note that the variation range is set as in the case where the slope start is used in end point detection.

When the slope end is used in end point detection, end point detection can be performed a plurality of number of times by sequentially setting new origins and variation ranges, as when the slope start is used in end point detection.

As described above, no direct comparison with threshold values is performed in determining the end point, and predetermined values obtained from the information in the averaging time of plasma processing are used in the end point determination. Consequently, it is possible to well remove drift variations which cannot be removed by conventional end point detection methods using two wavelengths. Therefore, the end point can be accurately detected even if the S/N (signal-to-noise ratio) is low. Note that the end point of actual plasma processing can be the position of either the slope start or the slope end. This selection is appropriately performed in accordance with the purpose and conditions of the plasma processing.

The end point detection method of the present invention can determine the slope start and the slope end in the same manner as described above as shown in FIG. 7B even when the waveform of a change in the emission intensity ratio with time rises near the end point as shown in FIG. 7A. It is to be understood that the resulting curve in this case largely protrudes into the first quadrant in the coordinate system.

When holes are to be formed by etching two different kinds of films, e.g., when an $SiO_2$ film 5 and an $Si_3N_4$ film 6 sequentially formed on a silicon substrate 4 are to be etched as shown in FIG. 8, the waveform of a change in the emission intensity ratio with time rises near the first end point or the end point in the first step and lowers near the second end point or the end point in the second step as shown in FIG. 9A. If this is the case, as shown in FIG. 9B, after the first end point is detected as above, a point at which the position of the ratio (A/A') and the derivative (d(A/A')/dt) of the ratio in the graph again intersects the abscissa of the graph is used as a new origin $O_2$. Another predetermined region (variation range) $R_2$ is set from a predetermined value of the ratio (A/A') and a predetermined value of the derivative (d(A/A')/dt) of the ratio calculated from the variance information. The ratio (A/A') and the derivative (d(A/A')/dt) of the ratio are obtained by using the emission detection information of the first and second active species. The second end point (slope start) of the plasma processing is determined when the position of the ratio (A/A') and the derivative (d(A/A')/dt) of the ratio thus obtained deviates from the predetermined region $R_2$. Note that in FIG. 9B, reference symbols $O_1$ and $R_1$ denote an origin and a variation range, respectively, when the first end point is detected. Note also that the second slope start and slope end are determined in the same manner as above.

As a consequence, it is possible to recognize the end point of the etching for forming a hole in the $Si_3N_4$ film 6 and the end point of the subsequent etching for forming a hole in the $SiO_2$ film 5.

Figure 10:
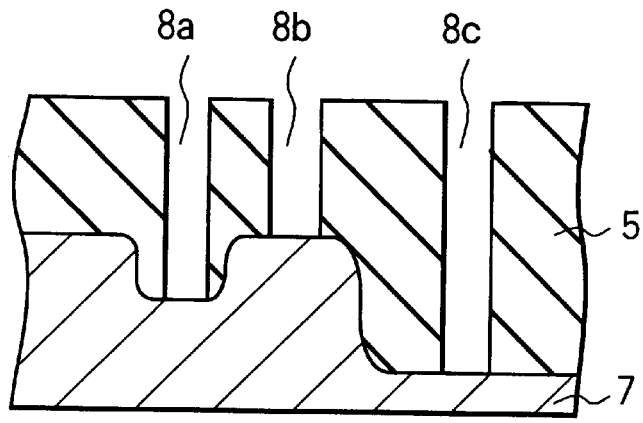
FIG. 10 is a sectional view showing another example of an object to be etched.
Figure 11A:
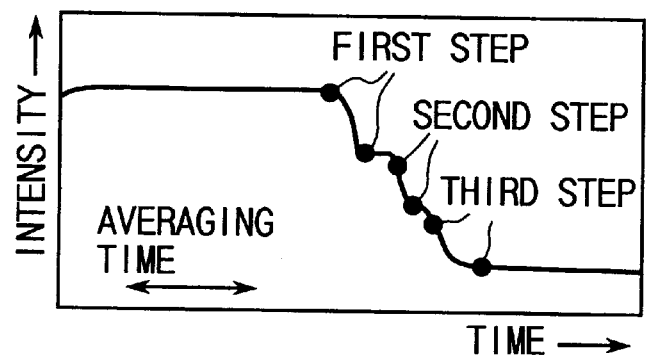
FIG. 11A is a graph showing still another example of the changes in the emission intensity (ratio) and the slope (derivative) with time.
Figure 11B:
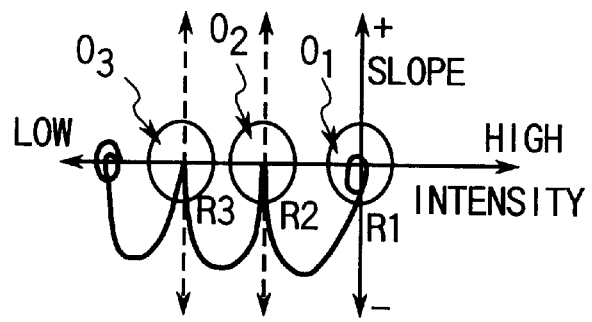
FIG. 11B is a graph in which the emission intensity (ratio) and the slope (derivative) shown in FIG. 11A are plotted on the abscissa and the ordinate, respectively.

This technique of repeating the determination of the slope start and the slope end by performing origin movement as described above is also applicable to a case in which, as shown in FIG. 10, holes 8a to 8b having different aspect ratios are to be formed in an $SiO_2$ film 5 which is formed on a substrate 7 with steps and has partially different thicknesses. Even in a case like this, as shown in FIGS. 11A and 11B, the slope start and the slope end can be determined a plurality of number of times by performing origin movement as described above, and the end point of etching processing in each step can be accurately detected. In FIG. 11B, reference symbol $O_1$ denotes an origin when the first end point or the end point in the first step is detected; $O_2$, an origin when the second end point or the end point in the second step is detected; $O_3$, an origin when the third end point or the end point in the third step is detected; $R_1$, a variation range when the first end point is detected; $R_2$, a variation range when the second end point is detected; and $R_3$, a variation range when the third end point is detected.

An embodiment performed to clarify the effect of the plasma processing end point detection method of the present invention will be described below.

Figure 12:
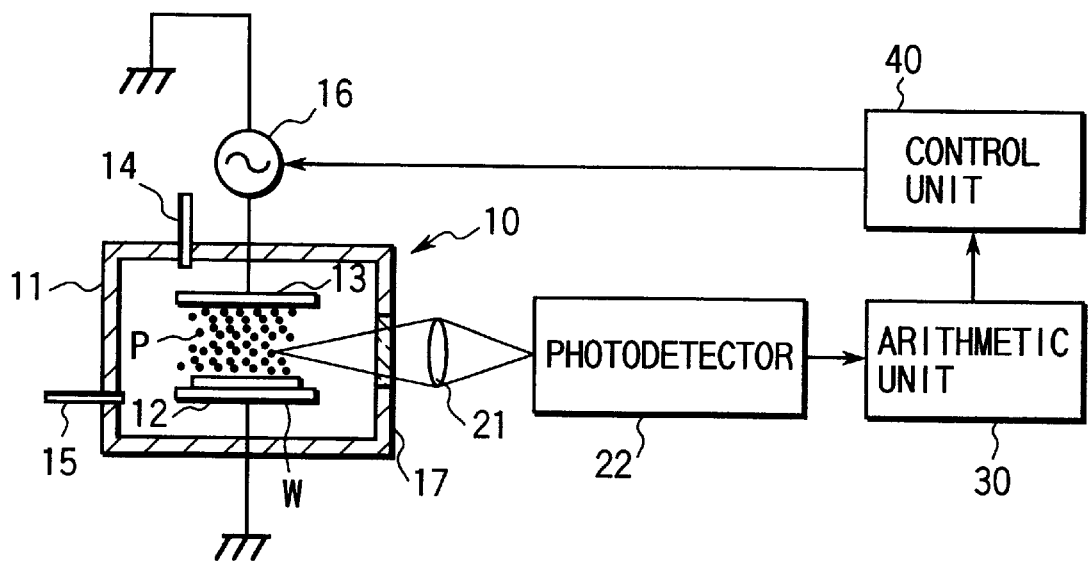
FIG. 12 is a view schematically showing a plasma etching system including an end point detecting apparatus of the present invention.

FIG. 12 is a view schematically showing the arrangement of a plasma processing system, e.g., a plasma etching system including an end point detecting apparatus according to the present invention. A plasma processing system 10 includes a processing chamber 11, a lower electrode 12, and an upper electrode 13. The processing chamber 11 is made from a conductive material such as aluminum. The lower electrode 12 is disposed in the processing chamber 11 and also serves as a table on which a semiconductor wafer W as an object to be processed is placed. The upper electrode 13 is disposed above and spaced apart from the lower electrode 12. A plasma generation region is defined between these electrodes.

A gas supply pipe 14 for supplying a processing gas, e.g., a fluorocarbon-based etching gas such as $CF_4$ is connected to the upper portion of the processing chamber 11. An exhaust pipe 15 for exhausting a production gas is connected to a side wall of the processing chamber 11. The lower electrode 12 is grounded and constantly held at the ground potential. The upper electrode 13 is connected to an RF power supply 16. This RF power supply 16 applies an RF power to cause discharge between the lower electrode 12 and the upper electrode 13, thereby activating the etching gas and generating a plasma P made from active species such as radical species or ionic species in the plasma generation region.

A monitor window 17 made from a transparent material such as quartz glass is adhered to a side wall of the processing chamber 11. The emission spectrum of the plasma P is transmitted through this window 17, and the progress of the etching is monitored by analyzing the transmitted light. A lens 21 for condensing the transmitted light is disposed outside the window 17. A photodetector 22 for detecting and photoelectrically converting the light condensed by the lens 21 is arranged behind the lens 21. This photodetector 22 includes, e.g., a pair of interference filters or spectroscopes and a pair of photomultipliers or photodiodes. Light having two specific wavelengths is divided by the interference filters or spectroscopes, and the divided light components of specific wavelengths are photoelectrically converted and transmitted as electrical signals representing changes in the emission intensities with time. On the basis of the two electrical signals transmitted from the photodetector 22 and corresponding to changes in the emission intensities with time, an arithmetic unit 30 (to be described later) detects the end point of the etching. When detecting the end point of the etching, the arithmetic unit 30 sends a control signal to a control unit 40 and controls the plasma processing system 10 via this control unit 40, i.e., stops the operation of the RF power supply 16 and ends the etching.

The position of the lens 21 can be properly moved vertically by a lens moving means (not shown). For example, when a film formed on a semiconductor substrate is to be plasma-etched for hole formation, if light reflected by the upper surface of the film and light reflected by the lower surface (the interface between the semiconductor substrate and the film) of the film enter the photodetector 22 while interfering with each other in detection of an emission spectrum having a specific wavelength, it may become impossible to accurately detect the emission intensity of the emission spectrum. To prevent the incidence of this interference light, the focal point of the lens can be moved by the lens moving means in this embodiment.

Figure 13:
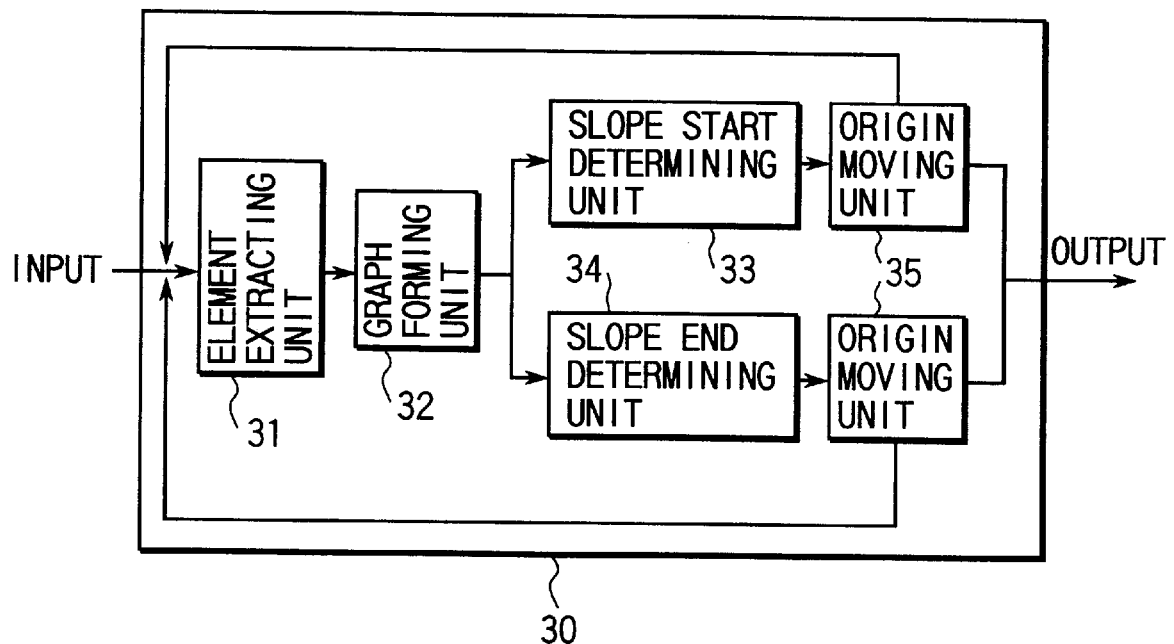
FIG. 13 is a view for explaining the end point detecting apparatus in the plasma etching system shown in FIG. 12.

The arithmetic unit 30 for performing end point detection according to the present invention will be described below. As shown in FIG. 13, the arithmetic unit 30 includes an element extracting unit 31, a graph forming unit 32, a slope start determining unit 33, and a slope end determining unit 34. The element extracting unit 31 arithmetically operates the information of input signals from the photodetector 22, i.e., a signal representing a change in the emission intensity of light having a first specific wavelength and a signal representing a change in the emission intensity of light having a second specific wavelength. The element extracting unit 31 then extracts, i.e., calculates the ratio of the changes in the two emission intensities and the derivative (slope) of the ratio. In a graph in which the ratio (A/A') of the emission intensities is plotted on the abscissa, the derivative (d(A/A')/dt) of the ratio, i.e., the slope is plotted on the ordinate, and the intersection between the average value of the ratio (A/A') and the average value of the derivative (d(A/A')/dt) is the origin, the graph forming unit 32 plots the changes in the ratio and the derivative of the ratio with time calculated as above, thereby forming a graph as shown in FIG. 5. The slope start determining unit 33 determines the slope start from the formed graph, and the slope end determining unit 34 determines the slope end from the graph. In this preferred embodiment, origin moving units 35 are arranged on the output sides of the determining units 33 and 34 to move the origin in a graph formed when a stacked film or a film formed on a substrate with steps described earlier is to be processed. These origin moving units are driven only when the origin as described above is to be moved, and command the element extracting unit 31 to repeat a similar operation.

More specifically, the element extracting unit 31 performs the following arithmetic processing.

(1) On the basis of the emission detection information of the first and second active species in the designated period (averaging time), the approximate expression of linear function A of the first active species and the approximate expression of linear function B of the second active species are obtained in the relationship between the emission intensity and time.

(2) The affine approximate expression of linear function A' of the first active species is obtained by using the approximate expression of linear function A of the first active species and the approximate expression of linear function B of the second active species, i.e., by substituting the elapsed time component of the approximate expression of linear function B of the second active species into the elapsed time component of the approximate expression of linear function A of the first active species.

(3) From the approximate expression of linear function A of the first active species and the affine approximate expression of linear function A' of the first active species, the ratio (A/A') of the two and the derivative (d(A/A')/dt) of the ratio are obtained.

(4) The average values and dispersion values of the ratio (A/A') and the derivative (d(A/A')/dt) of the ratio in the averaging time are obtained.

The graph forming unit 32, the slope start determining unit 33, and the slope end determining unit 34 perform the respective processing steps as described above, thereby performing graph formation, slope start determination, and slope end determination, respectively.

The results of the slope start determination and the slope end determination are transmitted to the control unit 40. The etching processing is controlled by controlling, e.g., the RF power supply 16 via the control unit on the basis of the signal of the determination results. Note that the slope end determination result is supplied, where necessary, to the origin moving unit 35, and a signal indicating the result of origin movement is also supplied to the control unit 40.

A method in which an $SiO_2$ film formed on a silicon substrate is actually etched with $CF_4$ gas by using the plasma processing system (plasma etching system) having the above configuration will be described below. In this method, CO molecules produced by etching of $SiO_2$ are used as the first active species, and $CF_2^*$ molecules as an ionized etchant are used as the second active species. The CO molecules are analyzed with a spectroscope, and the $CF_2^*$ molecules are filtered through an optofilter. Note that the use emission wavelength of the CO molecule is about 219 nm, and the use emission wavelength of the $CF_2^*$ molecule is about 260 nm.

First, an optical signal detected by the photodetector 22 and filtered is converted into an electrical signal by a photoelectric converter (not shown), and the electrical signal is amplified by a preamplifier (not shown).

By adjusting the amplification factor of a preamplifier for an electrical signal of the CO molecule, an electrical signal of the CO molecule is amplified to the same level as the $CF_2^*$ molecule. In this stage, the both electrical signals are analog signals.

Subsequently, noise components with a frequency twice the sampling cycle or more, in this embodiment 20 Hz or more, are cut through a filter. Thereafter, the two electrical signals are sampled at a cycle of 0.1 sec. and converted into digital signals by an A/D converter.

These digital electrical signals are then smoothed by dynamic averaging. This method has a so-called low-pass filter effect, and relatively smooth signals containing no RF noise (i.e., random noise) can be obtained.

Figure 14:
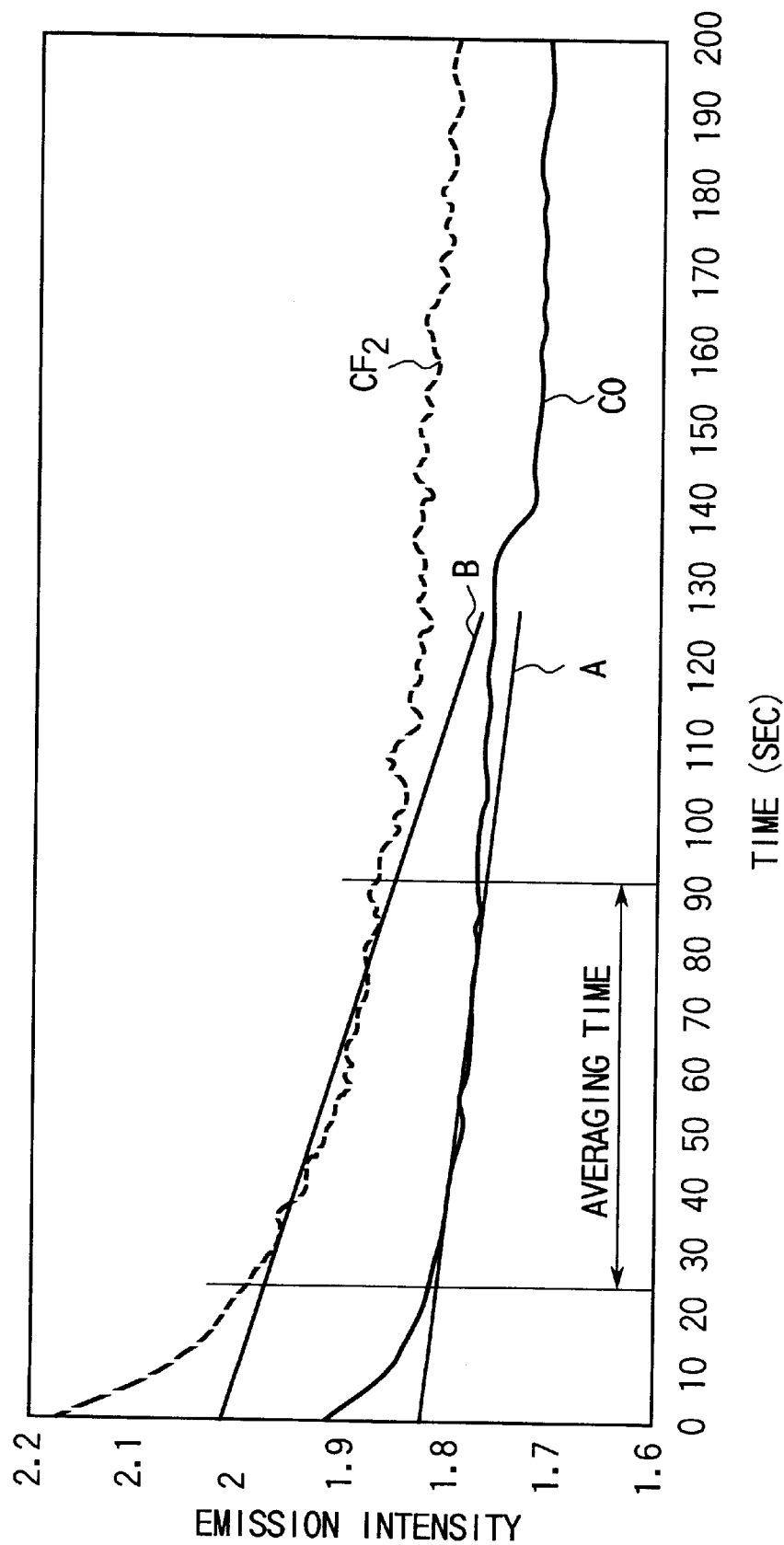
FIG. 14 is a graph showing changes in the emission intensities of a CO molecule and $CF_2^*$ with time.
Figure 15:
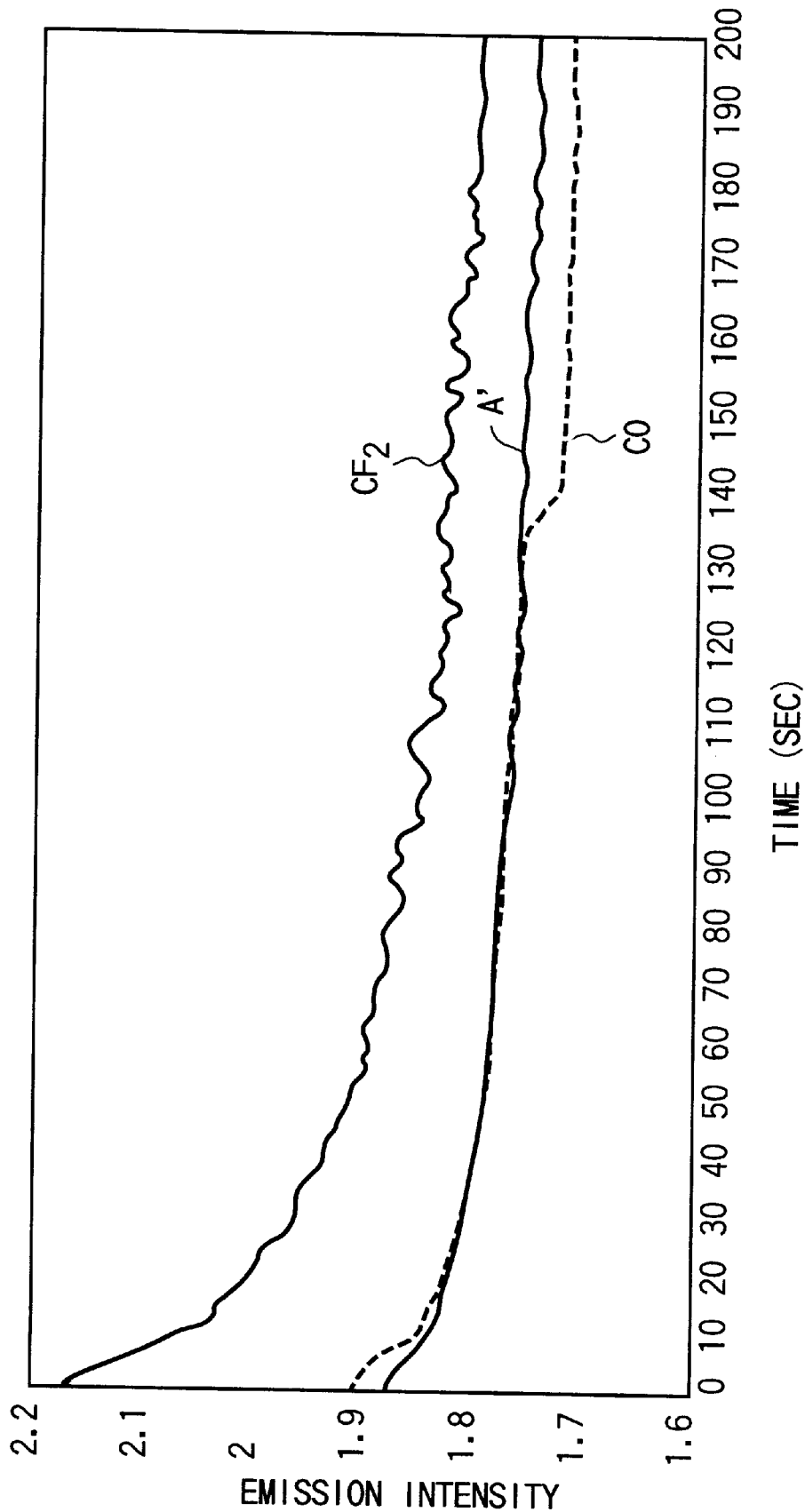
FIG. 15 is a graph showing changes in the emission intensities of a CO molecule and $CF_2^*$ with time after arithmetic operations.

Subsequently, the element extracting unit 31 obtains the approximate expression of linear function A of the CO molecule and the approximate expression of linear function B of the $CF_2^*$ molecule. FIG. 14 shows these changes in the emission intensities with time and straight lines indicating the linear expressions. Also, the affine approximate expression of linear function A' of the CO molecule is obtained from the approximate expression of linear function B of the $CF_2^*$ molecule by using these lines. FIG. 15 shows changes in the emission intensities with time corresponding to the expressions A, B, and A'.

Figure 16:
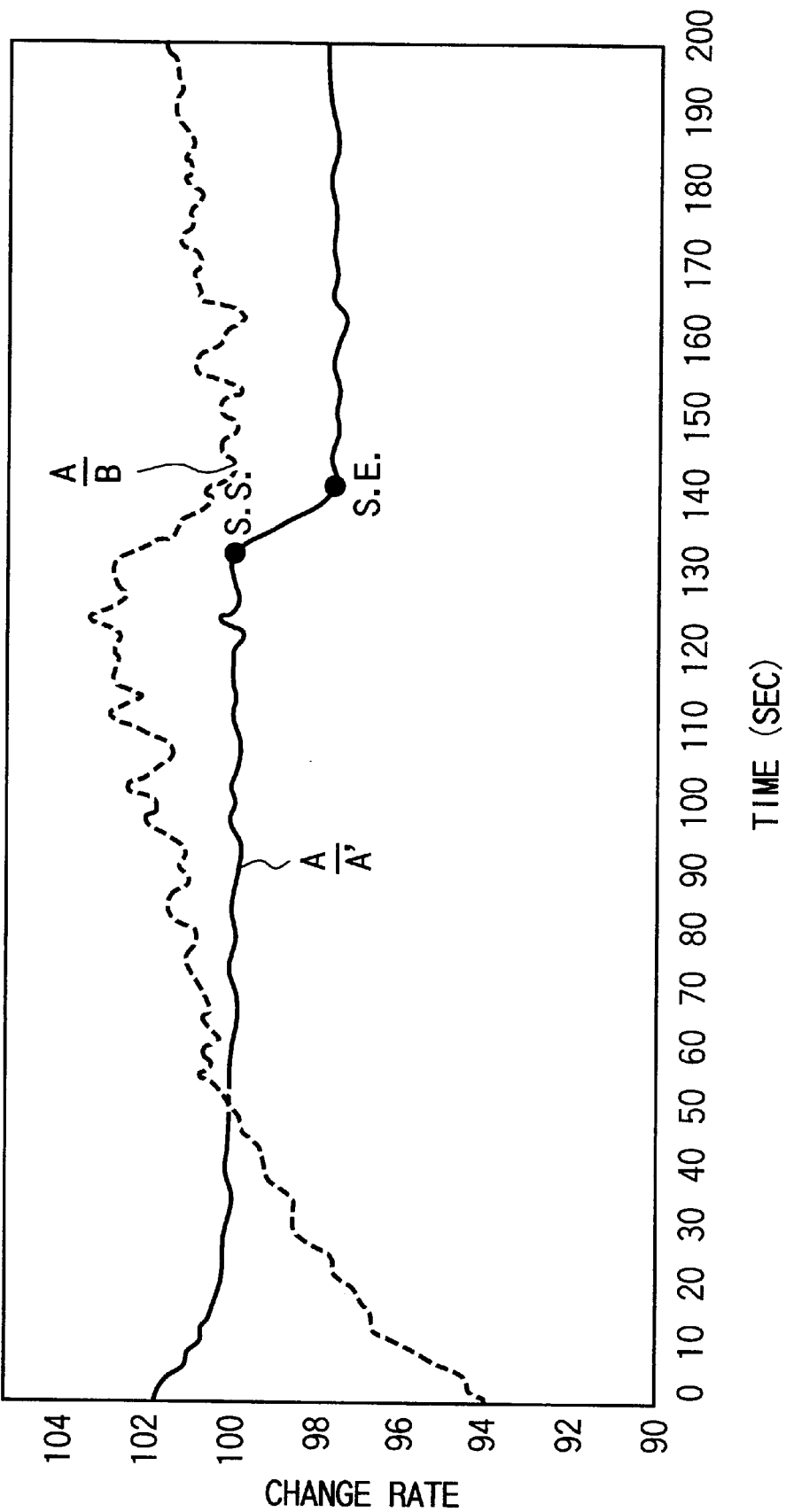
FIG. 16 is a graph showing changes in the change rate (ratio) of the emission intensities of a CO molecule and $CF_2^*$ with time.

Both the approximate expression of linear function A and the affine approximate expression of linear function A' represent the emission amounts (intensities) of the CO molecule, so the ratio (A/A') of these expressions and the derivative (d(A/A')/dt) of the ratio are obtained. FIG. 16 shows a change in the ratio (A/A') with time. For comparison, FIG. 16 also shows a change with time in a simple ratio (A/B) of the approximate expression of linear function A of the CO molecule to the approximate expression of linear function B of the $CF_2^*$ molecule. As is apparent from FIG. 16, the method of the present invention can accurately detect the end point because the waveform is flat before and after the end point. When the simple ratio (A/B) is used, on the other hand, the waveform does not stabilize, so the end point cannot be accurately detected due to drift variations.

Figure 17:
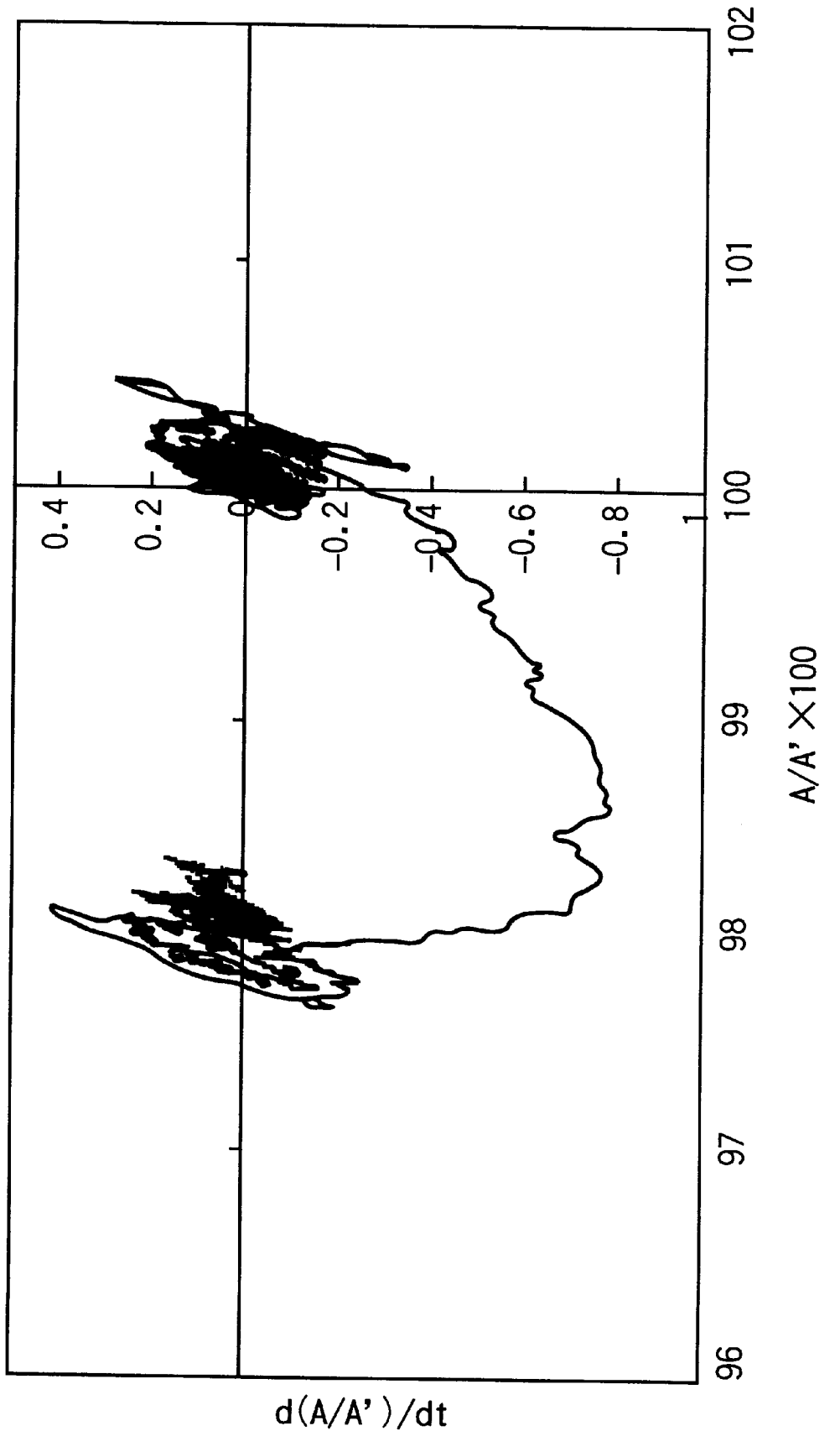
FIG. 17 is a graph in which the change rate (ratio) of the emission intensities of a CO molecule and $CF_2^*$ is plotted on the abscissa and the slope (derivative) is plotted on the ordinate.

Next, a graph is formed in which the ratio (A/A') is plotted on the abscissa, the derivative (d(A/A')/dt) of the ratio is plotted on the ordinate, and the average values of the ratio and the derivative of the ratio calculated from the information in the designated period (averaging time) are used as the origin. FIG. 17 shows a graph in which the ratio and the derivative of the ratio are plotted.

Additionally, the initial variation range in the graph is obtained from predetermined values of the ratio (A/A') and the derivative (d(A/A')/dt) of the ratio calculated from the information of the variances obtained in the averaging time.

Thereafter, a position (value) at which the end point is determined is set outside the variation range in the graph. The distance from the position to the origin is compared with the radius of the circle of the variation range, thereby determining the slope start by the slope start determining unit 33. That is, the ratio (A/A') and the derivative (d(A/A')/dt) of the ratio are obtained by using the emission detection information of the CO molecule and the $CF_2^*$ molecule during the processing after the averaging time, and the distance from the position to the origin in the graph is obtained and compared with the radius of the variation range obtained by the emission detection information in the averaging time.

More specifically, a root-sum-square value (D) of the differences between the ratio and the derivative of the ratio corresponding to the end point determination position and the respective average values (origin) is obtained. The slope start is determined when the ratio (D/C) of the root-sum-square value (D) to the radius (C) of the circle exceeds a preset threshold value.

On the other hand, the slope end is determined when the derivative of the ratio, i.e., the slope again comes close the abscissa. That is, the end point determination slope and a predetermined value based on the variance of the slope are compared to obtain ((slope—average value of slope)/ predetermined value). When this value becomes smaller than a preset threshold value, the slope end determining unit 34 determines the slope end.

In the end point detection method of the present invention described above, the emission amount (aperture ratio) can be improved to be three times (by 1% to 3%) as large as the conventional value.

In the above embodiment, CO molecules are used as the first active species, and $CF_2^*$ molecules are used as the second active species. However, the present invention is also applicable to a case in which other active species are used as the first and second active species.

Although plasma processing is etching in the above embodiment, the present invention is similarly applicable to a case in which plasma processing is processing using a plasma such as CVD (Chemical Vapor Deposition) or PVD (Physical Vapor Deposition).

In the above embodiment, experimental formulas approximating changes with time in the emission intensities of emission spectra at specific wavelengths of the first and second active species are approximate expressions of linear functions. However, it is evident to those skilled in the art that the experimental formulas are not restricted to these expressions. For example, when the emission intensities change with time along a portion of an ellipse or a hyperbola, expressions of quadratic functions can be used. That is, in the present invention the use of experimental formulas most approximating changes in the emission intensities is preferable to improve the accuracy of measurements.

To increase the sensitivity, it is preferable to use, as the first and second active species, an active species which decreases its emission intensity as shown in FIG. 4 and an active species which increases its emission intensity as shown in FIG. 7A at the end point of plasma processing after the designated period.

In the present invention as has been described above, no direct comparison with threshold values is performed, and predetermined values obtained from the information of the variances in the designated time of plasma processing are used in end point determination.

Consequently, it is possible to well remove drift variations which cannot be removed by conventional end point detection methods using two wavelengths. Therefore, the end point can be accurately detected even if the S/N ratio is low.

Since the end point of a plasma can thus be accurately detected, the emission amount (aperture ratio) can be improved to be three times as large as the conventional value.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

We claim:

1. A method of detecting an end point of plasma processing, comprising the steps of:

detecting, when processing using a plasma is performed for an object to be processed, emission intensities respectively having specific wavelengths of first and second active species in a designated period and after the designated period during the plasma processing, and outputting emission detection information;

obtaining an approximate expression A of the first active species and an approximate expression B of the second active species in a relationship between the emission intensity and time on the basis of the emission detection information;

obtaining an affine approximate expression A' of the first active species by using the approximate expression A of the first active species and the approximate expression B of the second active species;

obtaining a ratio (A/A') of the approximate expression A of the first active species to the affine approximate expression A' of the first active species and a derivative (d(A/A')/dt) of the ratio;

obtaining average values and variances of the ratio (A/A') and the derivative (d(A/A')/dt) of the ratio in the designated period;

setting a predetermined region from a predetermined value of the ratio (A/A') and a predetermined value of the derivative (d(A/A')/dt) of the ratio calculated from information of the variances in a graph in which the ratio (A/A') is plotted on an abscissa, the derivative (d(A/A')/dt) of the ratio is plotted on an ordinate, and an intersection between the average value of the ratio (A/A') and the average value of the derivative (d(A/A')/dt) of the ratio in the designated period is an origin; and obtaining the ratio (A/A') and the derivative (d(A/A')/dt) of the ratio by using the emission detection information of the first and second active species during the processing after the designated period, and determining an end point of the plasma processing when a position of the ratio (A/A') and the derivative (d(A/A')/dt) of the ratio thus obtained deviates from the predetermined region in the graph.

2. A method according to claim 1, wherein the predetermined region is set by a root-sum-square value $r_1$ of the predetermined value of the ratio (A/A') and the predetermined value of the derivative (d(A/A')/dt) of the ratio calculated from the variance information in the designated period.

3. A method according to claim 1, wherein a maximum value of differences between the ratio (A/A') and the average value of the ratio is used as the predetermined value of the ratio calculated from the variance information, and a maximum value of differences between the derivative (d(A/A')/dt) of the ratio and the average value of the derivative of the ratio is used as the predetermined value of the derivative of the ratio.

4. A method according to claim 1, wherein the step of determining the end point of the plasma processing comprises the steps of comparing the root-sum-square value $r_1$ of the predetermined value of the ratio (A/A') and the predetermined value of the derivative (d(A/A')/dt) of the ratio calculated from the variance information in the designated period with a distance $r_2$ from the position of the ratio (A/A') and the derivative (d(A/A')/dt) of the ratio in the graph to the origin, and determining the end point of the plasma processing when the distance $r_2$ exceeds the dispersion root-sum-square value $r_1$.

5. A method according to claim 1, wherein the step of determining the end point of the plasma processing comprises the steps of calculating a root-sum-square value $r_1$ of the predetermined value of the ratio (A/A') and the predetermined value of the derivative (d(A/A')/dt) of the ratio calculated from the variance information in the designated period, and determining the end point of the plasma processing when both values of an abscissa component and an ordinate component of coordinates in the graph exceed the root-sum-square value $r_1$ of the predetermined values.

6. A method according to claim 1, further comprising the steps of setting another predetermined region from the predetermined value of the ratio (A/A') and the predetermined value of the derivative (d(A/A')/dt) of the ratio by using a point, at which the position of the ratio (A/A') and the derivative (d(A/A')/dt) of the ratio in the graph again intersects the abscissa of the graph, as the origin, obtaining the ratio (A/A') and the derivative (d(A/A')/dt) of the ratio by using the emission detection information of the first and second active species during the processing after the designated period, and determining another end point of the plasma processing when the position of the ratio (A/A') and the derivative (d(A/A')/dt) of the ratio thus obtained deviates from the predetermined region.

7. A method according to claim 1, wherein the step of obtaining the approximate expression A of the first active species and the approximate expression B of the second active species is the step of obtaining an approximate expression of linear function A of the first active species and an approximate expression of linear function B of the second active species, the step of obtaining the affine approximate expression A' of the first active species is the step of obtaining an affine approximate expression of linear function A' of the first active species by using the approximate expression of linear function A of the first active species and the approximate expression of linear function B of the second active species, and the step of obtaining the ratio (A/A') and the derivative (d(A/A')/dt) of the ratio is the step of obtaining a ratio (A/A') of the approximate expression of linear function A of the first active species to the affine approximate expression of linear function A' of the first active species and a derivative (d(A/A')/dt) of the ratio.

8. A method of detecting an end point of plasma processing, comprising the steps of:

sequentially detecting, when processing using a plasma is performed for an object to be processed, emission intensities at specific wavelengths of emission from first and second active species in a designated period and after the designated period during the plasma processing by using photodetecting means, and outputting emission detection information;

obtaining an approximate expression A of the first active species and an approximate expression B of the second active species in a relationship between the emission intensity and time on the basis of the emission detection information in the designated period;

obtaining an affine approximate expression A' of the first active species by using the approximate expression A of the first active species and the approximate expression B of the second active species;

obtaining a ratio (A/A') of the approximate expression A of the first active species to the affine approximate expression A' of the first active species and a derivative (d(A/A')/dt) of the ratio;

obtaining average values and variances of the ratio (A/A') and the derivative (d(A/A')/dt) of the ratio in the designated period;

preparing a graph in which the ratio (A/A') is plotted on an abscissa, the derivative (d(A/A')/dt) of the ratio is plotted on an ordinate, and an intersection between the average value of the ratio (A/A') and the average value of the derivative (d(A/A')/dt) of the ratio in the designated period is an origin, and determining an end point of the plasma processing when a position of the ratio (A/A') and the derivative (d(A/A')/dt) of the ratio obtained by using the emission detection information of the first and second active species during the processing after the designated period in the graph deviates from the origin and again comes close to the abscissa.

9. A method of detecting an end point of plasma processing, comprising the steps of:

detecting, while processing using a plasma is performed for an object to be processed, emission intensities respectively at specific wavelengths of first and second active species generated by the plasma in a designated period and after the designated period during the processing, and outputting emission detection information;

obtaining an approximate expression A of the first active species and an approximate expression B of the second active species, each of which approximates a change in the emission intensity with passing of time and represents a straight line or a curve, on the basis of the emission detection information;

obtaining an affine approximate expression A' of the first active species by substituting an elapsed time of the approximate expression B of the second active species into an elapsed time of the approximate expression A of the first active species;

obtaining a ratio (A/A') of the approximate expression A of the first active species to the affine approximate expression A' of the first active species and a derivative (d(A/A')/dt) of the ratio;

obtaining average values and variances of the ratio (A/A') and the derivative (d(A/A')/dt) of the ratio in the designated period;

preparing a graph in which the ratio (A/A') is plotted on one axis of orthogonal coordinates, the derivative (d(A/A')/dt) of the ratio is plotted on the other axis of the orthogonal coordinates, and an intersection between the average value of the ratio (A/A') and the average value of the derivative (d(A/A')/dt) of the ratio in the designated period is an origin, and setting a predetermined region in the graph from a predetermined value of the ratio (A/A') and a predetermined value of the derivative (d(A/A')/dt) of the ratio calculated from information of the variances; and obtaining the ratio (A/A') and the derivative (d(A/A')/dt) of the ratio by using the emission detection information of the first and second active species during the processing after the designated period, and determining an end point of the plasma processing when a position of the ratio (A/A') and the derivative (d(A/A')/dt) of the ratio thus obtained deviates from the predetermined region in the graph.

10. A method according to claim 9, wherein active species which respectively decrease and increase emission intensities at the end point of the plasma processing after the designated period are used as the first and second active species, respectively.

11. An apparatus for detecting an end point of plasma processing, comprising:

photodetecting means for detecting, when processing using a plasma is performed for an object to be processed, changes with time in emission intensities at specific wavelengths of first and second active species generated by the plasma, and outputting emission detection information;

arithmetic means for obtaining an approximate expression A of the first active species and an approximate expression B of the second active species in a relationship between the emission intensity and time on the basis of the emission detection information in the designated period, obtaining an affine approximate expression A' of the first active species by using the approximate expression A of the first active species and the approximate expression B of the second active species, obtaining a ratio (A/A') of the approximate expression A of the first active species to the affine approximate expression A' of the first active species and a derivative (d(A/A')/dt) of the ratio, and obtaining average values and variances of the ratio (A/A') and the derivative (d(A/A')/dt) of the ratio in the designated period;

graph forming means for forming a graph in which the ratio (A/A') is plotted on an abscissa, the derivative (d(A/A')/dt) of the ratio is plotted on an ordinate, and an intersection between the average value of the ratio (A/A') and the average value of the derivative (d(A/A')/dt) of the ratio is an origin; and determining means for setting a predetermined region from a predetermined value of the ratio (A/A') and a predetermined value of the derivative (d(A/A')/dt) of the ratio calculated from information of the variances, obtaining the ratio (A/A') and the derivative (d(A/A')/dt) of the ratio by using the emission detection information of the first and second active species during the processing after the designated period, and determining an end point of the plasma processing when a position of the ratio (A/A') and the derivative (d(A/A')/dt) of the ratio thus obtained deviates from the predetermined region in the graph.

* * * * *